United States Patent
Noack et al.

(10) Patent No.: US 8,216,478 B2
(45) Date of Patent: Jul. 10, 2012

(54) METHOD AND APPARATUS FOR MONITORING THE SUPPLY OF REPLACEMENT FLUID DURING AN EXTRACORPOREAL TREATMENT OF BLOOD

(75) Inventors: Joachim Noack, Bad Neustadt (DE); Joerg Dreyhsig, St. Wendel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 270 days.

(21) Appl. No.: 12/741,065

(22) PCT Filed: Oct. 31, 2008

(86) PCT No.: PCT/EP2008/009192
§ 371 (c)(1),
(2), (4) Date: May 3, 2010

(87) PCT Pub. No.: WO2009/056325
PCT Pub. Date: May 7, 2009

(65) Prior Publication Data
US 2010/0264086 A1 Oct. 21, 2010

(30) Foreign Application Priority Data
Nov. 3, 2007 (DE) .......................... 10 2007 052 571

(51) Int. Cl.
*B01D 61/30* (2006.01)
*B01D 61/14* (2006.01)
*B01D 61/18* (2006.01)
*B01D 61/20* (2006.01)
*B01D 61/24* (2006.01)
*B01D 61/28* (2006.01)
*A61M 1/34* (2006.01)

(52) U.S. Cl. ........... 210/740; 210/85; 210/86; 210/96.1; 210/97; 210/143; 210/252; 210/257.1; 210/258; 210/321.6; 210/321.65; 210/645; 210/646; 210/647; 210/650; 210/739; 604/4.01; 604/6.09; 604/6.11; 604/28; 604/30

(58) Field of Classification Search ................. 210/645, 210/646, 647, 650, 739, 740, 85, 86, 96.2, 210/97, 143, 252, 257.1, 258, 321.6, 321.65; 604/4.01, 6.09, 6.11, 28, 30
See application file for complete search history.

(56) References Cited

FOREIGN PATENT DOCUMENTS
| | | |
|---|---|---|
| EP | 0 089 003 | 9/1983 |
| EP | 1 175 917 | 1/2002 |
| WO | WO 03/047656 | 6/2003 |

OTHER PUBLICATIONS

International Preliminary Report on Patentability for PCT/EP08/009192, mailed on Jun. 10, 2010.
PCT International Search Report and Written Opinion for PCT/EP08/009192, mailed on Mar. 17, 2009.

*Primary Examiner* — John Kim
(74) *Attorney, Agent, or Firm* — Kenyon & Kenyon LLP

(57) ABSTRACT

An apparatus and a method for monitoring the supply of replacement fluid during an extracorporeal treatment of blood is disclosed. Detection of the supply of replacement fluid upstream or downstream of the dialyser or filter is based on a measurement of the optical or physical density of the blood or of a constituent of blood in the extracorporeal circulation. To detect pre- or post-dilution, the blood flow rate and/or the replacement rate and/or the flow rate of the fluid removed from the blood through the dialyser membrane is altered, and the density of the blood or of the constituent of blood is measured upstream and/or downstream of the dialyser. Additionally, an apparatus for treating blood with an apparatus for monitoring the supply of replacement fluid is disclosed.

24 Claims, 2 Drawing Sheets

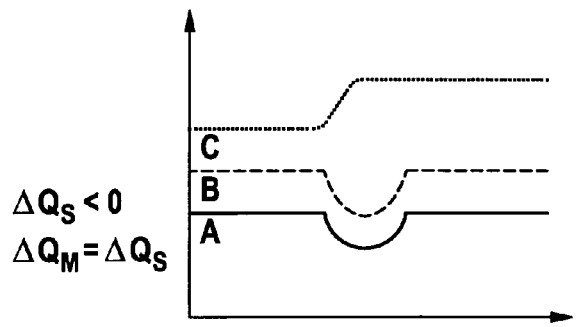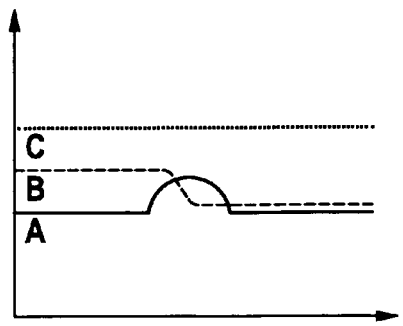
Fig. 2A                Fig. 2B
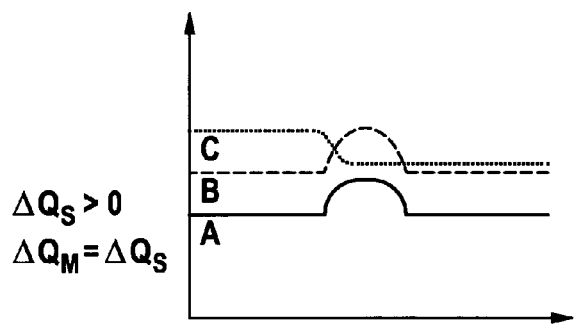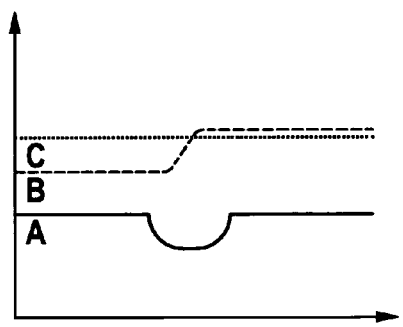
Fig. 3A                Fig. 3B
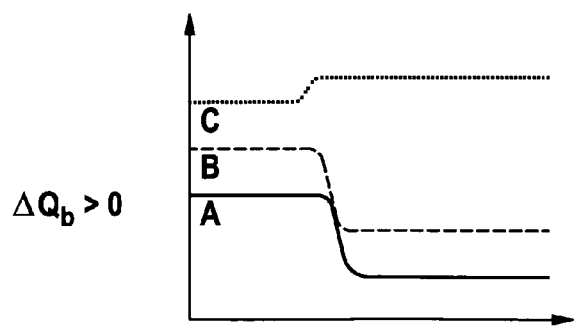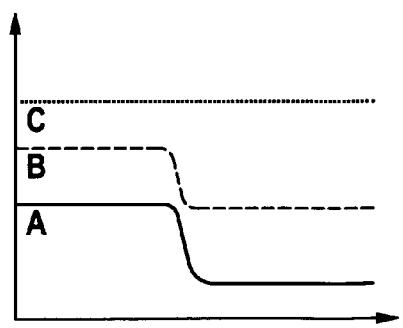
Fig. 4A                Fig. 4B

METHOD AND APPARATUS FOR MONITORING THE SUPPLY OF REPLACEMENT FLUID DURING AN EXTRACORPOREAL TREATMENT OF BLOOD

FIELD OF THE INVENTION

The present invention relates to a method for monitoring the supply of substitution fluid for an apparatus for extracorporeal blood treatment with an extracorporeal blood circuit, which comprises a first chamber of a dialyzer or filter divided by a membrane into the first chamber and a second chamber, and a fluid system which comprises the second chamber of the dialyzer or filter. Moreover, the present invention relates to a device for monitoring the supply of substitution fluid for an apparatus for extracorporeal blood treatment as well as an extracorporeal blood treatment apparatus with a monitoring device for the supply of substitution fluid.

BACKGROUND

Various methods for extracorporeal blood treatment or cleaning are used to remove substances usually eliminated with urine and for fluid withdrawal. In hemodialysis, the patient's blood is cleaned outside the body in a dialyzer. The dialyzer comprises a blood chamber and a dialyzing fluid chamber, which are separated by a semipermeable membrane. During the treatment, the patient's blood flows through the blood chamber. In order to clean the blood effectively from substances usually eliminated with urine, fresh dialyzing fluid flows continuously through the dialyzing fluid chamber.

Whereas the transport of the lower-molecular weight substances through the membrane of the dialyzer is essentially determined by the concentration differences (diffusion) between the dialyzing fluid and the blood in the case of hemodialysis (HD), substances dissolved in the plasma water, in particular higher-molecular weight substances, are effectively removed by a high fluid flow (convection) through the membrane of the dialyzer in the case of hemofiltration (HF). In hemofiltration, the dialyzer functions as a filter. Hemodiafiltration (HDF) is a combination of the two processes.

In hemo(dia)filtration, part of the serum drawn off through the membrane of the dialyzer is replaced by a sterile substitution fluid, which is generally fed to the extracorporeal blood circuit either upstream of the dialyzer or downstream of the dialyzer. The supply of substitution fluid upstream of the dialyzer is also referred to as pre-dilution and the supply downstream of the dialyzer as post-dilution.

Apparatuses for hemo(dia)filtration are known, wherein the dialyzing fluid is prepared online from fresh water and dialyzing fluid concentrate and the substitution fluid is prepared online from the dialyzing fluid.

In the known hemo(dia)filtration apparatuses, the substitution fluid (substituate) is fed to the extracorporeal blood circuit from the fluid system of the machine via a substituate supply line. With pre-dilution, the substituate line leads to a connection point on the arterial blood line upstream of the dialyzer or filter, whereas with post-dilution the substituate line leads to a connection point on the venous blood line downstream of the dialyzer or filter. The substituate line comprises for example a connector with which it may be connected either to the venous or arterial blood line. In order to interrupt the fluid supply, a clamp or suchlike is provided on the substituate line. A hemo(dia)filtration apparatus of this kind is known for example from European Patent Publication No. EP 0 189 561.

The effectiveness of the blood treatment depends on whether the substitution fluid is fed to the extracorporeal blood circuit upstream or downstream of the dialyzer or filter. A knowledge of the mode of treatment, i.e., pre- or post-dilution, is therefore important.

European Patent Publication No. EP 1 348 458 A1 describes a method and a device for monitoring the supply of substitution fluid for an extracorporeal blood treatment apparatus. The propagation time of the pressure waves of a substituate pump disposed in the substituate line is measured in order to detect the supply of substitution fluid upstream or downstream of the dialyzer or filter. The supply of substituate upstream or downstream of the dialyzer or filter is detected on the basis of the propagation measurement. The known method requires the use of a substituate pump generating pressure waves.

There is known from German Patent Publication DE 10 2004 023 080 A1 a device for monitoring the supply of substitution fluid, wherein the supply of substituate upstream or downstream of the dialyzer or filter is detected on the basis of the change in the pressure, for example on the basis of a sudden pressure rise and/or pressure drop after the substituate pump is switched off or switched on. The known method requires the use of a substituate pump generating pressure waves.

A goal of example embodiments of the present invention is to provide a method for monitoring the supply of substitution fluid, which permits the detection of pre- or post-dilution with a high degree of reliability. Moreover, it is a goal of example embodiments of the present invention to provide a device for monitoring the supply of substitution fluid, with which the pre- and post-dilution may be reliably detected. A further goal of example embodiments of the present invention is to create an extracorporeal blood treatment apparatus with such a monitoring device.

SUMMARY

The method according to example embodiments of the present invention and the device according to example embodiments of the present invention for the detection of pre- or post-dilution is based on the measurement and monitoring of the density of the blood or a blood constituent in the extracorporeal circuit. When there is a change in substitution rate $Q_S$ at which substitution fluid is fed to the blood in the extracorporeal circuit, and/or blood flow rate $Q_B$ at which blood is fed to the first chamber of the dialyzer or filter and/or flow rate $Q_M$ at which fluid is withdrawn from the blood via the membrane of the dialyzer or filter, the density of the blood or the blood constituent in the extracorporeal blood circuit changes. It has been shown that the amount and/or the direction of the change, i.e., an increase or reduction in the density by a specific value, depends on whether the substitution fluid is fed to the blood upstream or downstream of the dialyzer or filter. It is then concluded that there is a pre-dilution or post-dilution on the basis of the change in the density of the blood or the blood constituent. Change in density is also understood in this sense to mean the change in concentration of a blood constituent such as for example hemoglobin.

The method according to example embodiments of the present invention and the device according to example embodiments of the present invention in principle require only the single change in substitution rate $Q_S$ and/or blood flow rate $Q_B$ and/or flow rate $Q_M$ at which fluid is withdrawn from the blood via the membrane of the dialyzer or filter. Since the pre- or post-dilution is to be monitored during the blood treatment, which is preferably to be carried out at specific fluid rates $Q_S$, $Q_B$ and/or $Q_M$, a preferred embodiment makes provision, after the reduction or increase in at least one of the three fluid rates by a preset amount for a preset time interval, which should be as short as possible, for an increase or reduction again after the lapse of the preset time interval by a preset amount, which in particular corresponds to the amount by which the corresponding fluid rate or the fluid rates has or have been previously reduced or increased, so that the blood treatment may be continued at the same fluid rates. Flow rate $Q_M$ withdrawn from the blood is reduced or increased preferably simultaneously in the same time interval preferably by the same amount and, after the lapse of the preset time interval, preferably increased or reduced again by the same amount as substitution rate $Q_S$.

When mention is made below of a change in the flow rate, this may also be understood to mean a reduction in the flow rate by an amount such that the flow rate is zero, i.e., the flow is interrupted.

The amount by which a flow rate is reduced or increased is in principle irrelevant for the detection of pre- or post-dilution. The decisive factor, however, is that a change in the density can be detected selectively for pre- and post-dilution with sufficient reliability.

The method according to example embodiments of the present invention and the device according to example embodiments of the present invention provide different embodiments, which differ from one another by the point of the extracorporeal blood circuit at which the density of the blood or the blood constituent is measured.

A pre- or post-dilution may be detected by a measurement of the density downstream of the point of the extracorporeal blood circuit at which substitution fluid is fed to the blood circuit in the case of a pre-dilution and upstream of the first chamber of the dialyzer or filter. It is also possible to detect a pre- or post-dilution by a measurement of the density downstream of the first chamber of the dialyzer or filter and upstream of the point of the blood circuit at which substitution fluid is fed to the blood circuit in the case of post-dilution. The density may also be detected by a measurement downstream of the point of the blood circuit at which substitution fluid is fed to the blood circuit in the case of post-dilution. It may be decisive that the density is measured immediately after the change in the respective flow rate, since a change in the density may be detected only within a specific time interval, depending on the measurement position. The reason is that, in these cases, the density may reassume its original value after the lapse of this time interval.

It has been shown that the change in substitution rate $Q_S$, with a simultaneous change in flow rate $Q_M$ at which fluid is removed from the blood via the membrane of the dialyzer or filter, leads to notably different changes in the density at different points of the extracorporeal circuit. For example, the density may increase or decrease depending on a pre- or post-dilution.

In a first example embodiment, substitution rate $Q_S$ is reduced by a preset amount and the density is measured in the blood circuit downstream of the point of the blood circuit at which substitution fluid is fed to the blood circuit in the case of pre-dilution and upstream of the first chamber of the dialyzer or filter. The density of the blood or blood constituent before the reduction in substitution rate $Q_S$ and after the reduction in substitution rate $Q_S$ are then compared with one another, it being concluded that there is a supply of substitution fluid upstream of the dialyzer or filter if the density after the reduction of the substitution rate has increased by a preset amount. If the density of the blood after the reduction in the substitution rate has not increased by a preset amount, it is concluded on the other hand that there is a supply of substitution fluid downstream of the dialyzer or filter.

The method according to the invention and the device according to the invention do not in principle require the measurement of the density of the blood both before and after the reduction in the substitution rate. It may, in principle, be sufficient to measure the density only after the reduction in the substitution rate, in order to compare the measured value with a characteristic threshold value.

A particularly preferred example embodiment with a particularly significant change in the density of the blood provides for a measurement of the density of the blood or blood constituent in the blood circuit downstream of the point of the blood circuit at which substitution fluid is fed to the blood circuit in the case of post-dilution. After a comparison of the density before and after the reduction in substitution rate $Q_S$ and preferably a simultaneous reduction in flow rate $Q_M$, it is concluded that there is a supply of substitution fluid upstream of the dialyzer or filter if the density after the reduction in substitution rate $Q_S$ has diminished by a preset amount. It is concluded that there is a supply of substitution fluid downstream of the dialyzer or filter if the density after the reduction in substitution rate $Q_S$ has increased by a preset amount.

The increase in the density of the blood or the blood constituent in the case of post-dilution is due to the fact that, immediately after the reduction in substitution rate $Q_S$ at which the substitution fluid is fed to the blood and the simultaneous reduction in fluid rate $Q_M$ at which fluid is withdrawn from the blood via the membrane of the dialyzer or filter, a corresponding quantity of fluid has also been withdrawn via the membrane from the blood now flowing out of the dialyzer. The blood flowing out of the dialyzer or filter is thus thickened immediately after the reduction in rates $Q_S$ and $Q_M$. A reduction in the quantity of the substitution fluid fed to the blood after the passage through the dialyzer (post-dilution) therefore leads directly to an increase in the density of the blood or the blood constituent in the blood circuit downstream of the dialyzer. When, on the other hand, rates $Q_S$ and $Q_M$ are reduced in the case of pre-dilution, the blood present in the dialyzer or filter has already been diluted by the previous inflow of substitution fluid. Since the filtration in the dialyzer corresponding to the substituate flow is reduced or does not take place, the density of the blood flowing back to the patient diminishes. It is therefore concluded that there is a supply of substitution fluid upstream of the dialyzer or filter (pre-dilution) if the density of the blood or the blood constituent, after the reduction in substitution rate $Q_S$, has diminished by a preset amount or diminished by an amount which is greater than the preset threshold value.

On the basis of the increase or reduction in the density of the blood or blood constituent after the reduction in substitution rate $Q_S$, it is therefore possible to conclude with a high degree of reliability that there is a post- or pre-dilution. The increase or decrease in the density should however exceed a preset threshold value, in order for it to be possible to distinguish reliably between a change in the density of the blood due to a change in the flow rates and general density fluctuations of the blood.

An increase in substitution rate $Q_S$ at which fluid is withdrawn from the blood is also possible instead of a reduction in substitution rate $Q_S$. In this example embodiment, the density may be measured downstream of the point of the blood circuit at which substitution fluid is fed to the blood circuit in the case of pre-dilution and upstream of the first chamber of the dialyzer or filter. It is concluded that there is a supply of substitution fluid upstream of the dialyzer (pre-dilution) or filter if the density after the increase in the substitution rate has diminished by a preset amount, and it is concluded that there is a supply of substitution fluid downstream of the dialyzer or filter (post-dilution) if the density after the increase in the substitution rate has not diminished by a preset amount.

In this example embodiment, the density of the blood or the blood constituent in the blood circuit may alternatively also be measured downstream of the point of the blood circuit at which substitution fluid is fed to the blood circuit in the case of post-dilution. It can be concluded that there is a supply of substitution fluid upstream of the dialyzer or filter, preferably with a simultaneous increase in flow rate $Q_M$, if the density after the increase in substitution rate $Q_S$ has increased by a preset amount, and it is concluded that there is a supply of substitution fluid downstream of the dialyzer or filter if the density after the reduction in substitution rate $Q_S$ has diminished by a preset amount.

As the density of the blood, it is possible to measure both the physical density or mass density, which describes a mass distribution, as well as the optical density of the blood, which is a measure of the attenuation of radiation (for example light) in a medium, i.e., the blood.

For the method according to the invention, consideration may be given in particular to all measurement methods with which a measurement of the physical or optical density of the blood or one of its constituents is possible. For the measurement of the change in the density, a first example embodiment provides for a measurement of the propagation speed of ultrasound in the blood along a measuring distance, while an alternative example embodiment provides for the measurement of the attenuation of light in the blood along a measuring distance. The measurement equipment required for this is generally known to the person skilled in the art. Moreover, optical detectors for the detection of blood and ultrasound measuring distances for the detection of air are in any case generally present in the known dialysis apparatuses.

In a further particularly preferred example embodiment, a signal signaling the operational state of pre-dilution is generated when a pre-dilution is detected, whereas a signal signaling the operational state of post-dilution is generated when a post-dilution is detected. The signal for the pre- or post-dilution may control further devices provided in the blood treatment apparatus. For example, an intervention in the blood treatment may be made.

The device according to the invention for monitoring the supply of substitution fluid may be a component of a blood treatment apparatus or form a separate unit. Since the components required for the monitoring device are generally in any case present in the known blood treatment apparatuses, an integration into the blood treatment apparatuses is appropriate. The corresponding sensors for the density measurement may for example be used. A microprocessor control is also available. The outlay on equipment is therefore small.

The monitoring device according to the present invention comprises a control unit for controlling the substitution apparatus and the ultrafiltration apparatus for withdrawing ultrafiltrate via the dialyzer membrane, in such a way that corresponding flow rates $Q_S$ and $Q_M$ may be adjusted for the measurement. A measuring unit is used to measure the density of the blood or the blood constituent and an evaluation unit is used to detect the pre- or post-dilution on the basis of the density measurement.

The method according to the present invention and the apparatus according to the present invention may give the user not only an indication of the type of treatment, i.e., pre- or post-dilution, but also deviations between the actual and the desired type of treatment. Moreover, automatic documentation or an automatic limitation of the input parameters is possible. With the method according to the present invention and the apparatus according to the present invention, it is also possible to control other operational parameters of the blood treatment apparatus depending on the respective operational state.

Not only the change in the corresponding flow rates, but also other parameters have an influence on the duration of the change in density. For example, the volume of the blood chamber of the dialyzer and the volume of the hose line sections following the blood chamber have an influence on the duration of the change in density. In this respect, the volume of a partial section of the extracorporeal blood circuit may also be deduced using the density measurement. The level of the change in density depends on the enclosed volume of blood.

Example embodiments of the method according to the invention and of the blood treatment apparatus according to the invention are described in greater detail below by reference to the figures.

BRIEF DESCRIPTION OF THE DRAWINGS

FIGS. 2A and 2B show the time-related course of the density in the case of pre-dilution and post-dilution with a reduction in substitution rate $Q_S$ and flow rate $Q_M$, at which fluid is withdrawn from the blood via the membrane of the dialyzer or filter, by the same amount.

FIG. 3A and 3B show the time-related course of the density in the case of pre-dilution and post-dilution with an increase in substitution rate $Q_S$ and flow rate $Q_M$, at which fluid is withdrawn from the blood via the membrane of the dialyzer or filter, by the same amount.

FIG. 4A and 4B show the time-related course of the density in the case of pre-dilution and post-dilution with an increase in the blood flow rate.

DETAILED DESCRIPTION

Figure 1:
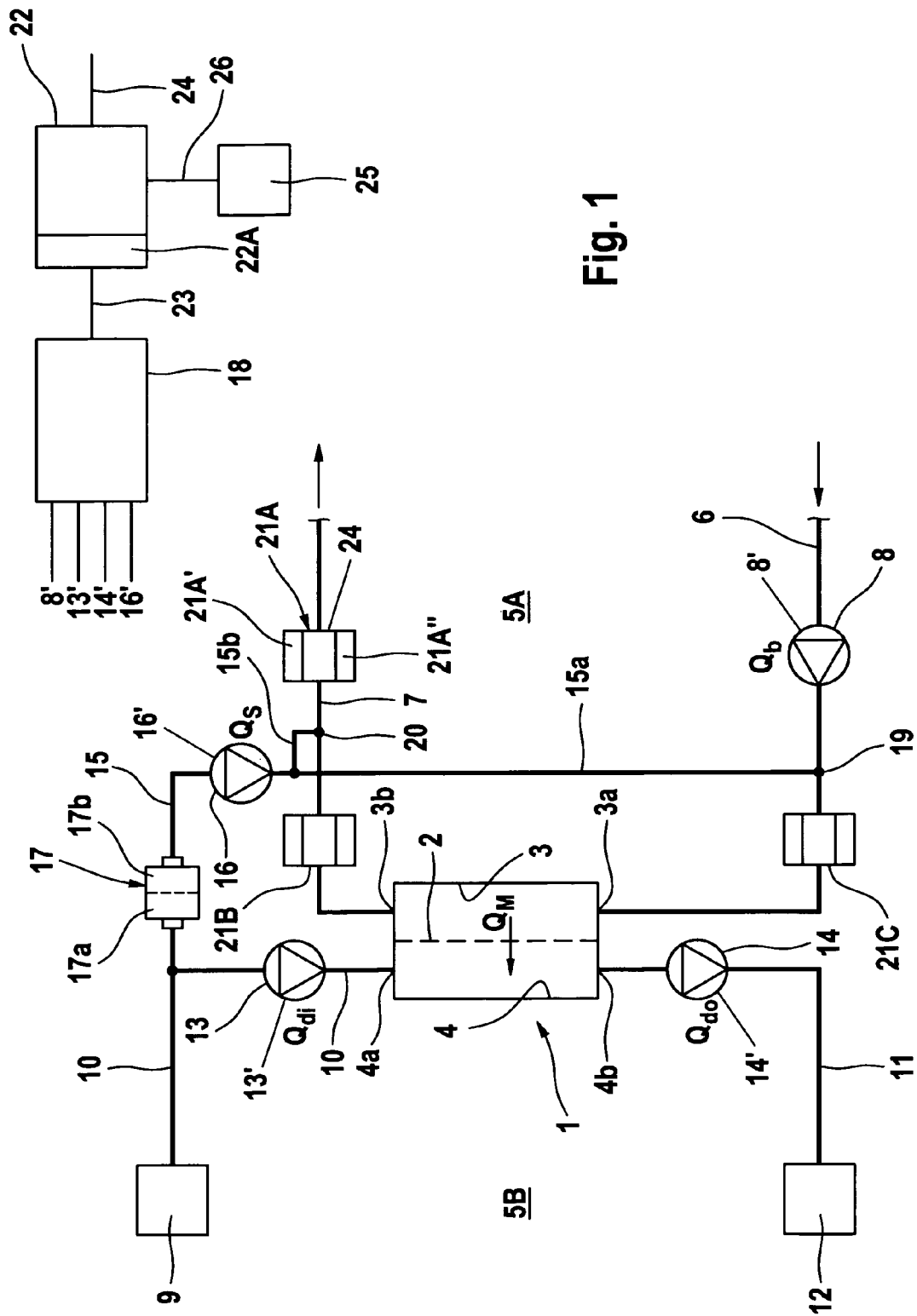
FIG. 1 shows an extracorporeal blood treatment apparatus with a device for monitoring the supply of substitution fluid, in particular for detecting pre- and post-dilution, in a very simplified schematic representation.

FIG. 1 shows, in a schematic representation, only the main components of a blood treatment apparatus that are relevant for the monitoring of the pre- or post-dilution. The present blood treatment apparatus is a hemo(dia)filtration apparatus, which comprises a dialyzer 1, which is divided by a semipermeable membrane 2 into a first chamber 3, through which blood flows and which is referred to in the following as the blood chamber, and a second chamber 4, through which dialyzing fluid flows and which is referred to in the following as the dialyzing fluid chamber. First chamber 3 is incorporated in an extracorporeal blood circuit 5A, while second chamber 4 is incorporated in dialyzing fluid system 5B of the hemo(dia)filtration apparatus.

Extracorporeal blood circuit 5A comprises an arterial blood line 6, which leads to inlet 3a of blood chamber 3, and a venous blood line 7, which leads away from outlet 3b of blood chamber 3 of dialyzer 1. The patient's blood is conveyed through blood chamber 3 of dialyzer 1 by an arterial blood pump 8, in particular a roller pump, which is disposed on arterial blood line 6. The blood pump feeds blood to blood chamber 3 of the dialyzer at a specific blood flow rate $Q_b$. Blood lines 6, 7 and dialyzer 3 form a disposable intended for one-off use, which is inserted into the dialysis apparatus for the dialysis treatment. An air separator (drip chamber) may be incorporated into the arterial and venous blood line in order to eliminate air bubbles.

The fresh dialyzing fluid is made available in a dialyzing fluid source 9. A dialyzing fluid supply line 10 leads from dialyzing fluid source 9 to an inlet 4a of dialyzing fluid chamber 4 of dialyzer 1. A dialyzing fluid discharge line 11 leads from outlet 4b of dialyzing fluid chamber 4 to a drain 12. A first dialyzing fluid pump 13 is incorporated in dialyzing fluid supply line 10 and a second dialyzing fluid pump 14 is incorporated in dialyzing fluid discharge line 11. First dialyzing fluid pump 13 conveys dialyzing fluid from the dialyzing fluid source at a specific dialyzing fluid supply rate $Q_{di}$ to inlet 4a of dialyzing fluid chamber 4, while second dialyzing fluid pump 14 conveys dialyzing fluid at a specific dialyzing fluid flow rate $Q_{do}$ from outlet 4b of dialyzing fluid chamber 4 to drain 12.

During the dialysis treatment, dialyzing fluid may be fed from dialyzing fluid system 5B as a substitution fluid to extracorporeal blood circuit 5A via a substitution fluid line 15, which branches off from dialyzing fluid supply line 10 upstream of first dialyzing fluid pump 13.

Substitution fluid line 15 comprises two line sections 15a and 15b, one line section 15a leading to arterial blood line 6 and the other line section 15b leading to venous blood line 7.

The substitution fluid is conveyed by means of a substituate pump 16, in particular a roller pump, into which substitution fluid line 15 is inserted. A sterile filter 17 divided into two chambers 17a, 17b is incorporated into substitution fluid line 15 upstream of the substituate pump. The substituate pump together with the respective lines and the sterile filter form the substitution device of the dialysis apparatus. In order to pinch off the two line sections 15a, 15b of substitution fluid line 15, shut-off elements, for example hose clamps, may be provided, which however are not represented for the sake of better clarity.

Blood pump 8, first and second dialyzing fluid pumps 13 and 14 and substituate pump 16 are connected via control lines 8', 13', 14', 16' to a central control and computing unit 18, from which the pumps are controlled taking account of the preset treatment parameters.

Blood pump 8 as well as first and second dialyzing fluid pumps 13 and 14 are operated in order to operate the hemo (dia)filtration apparatus as a hemodialysis apparatus, dialyzing fluid flowing through dialyzing fluid chamber 4 of dialyzer 1. Substituate pump 16 is operated in order to operate the hemo(dia)filtration apparatus as a hemodiafiltration apparatus, so that sterile dialyzing fluid flows as a substitution fluid via sterile filter 17 optionally to arterial admission point 19 downstream of pump 8 and upstream of blood chamber 3 (pre-dilution) or to venous admission point 20 downstream of the blood chamber (post-dilution). Operation of the hemo (dia)filtration apparatus solely as a hemofiltration apparatus is however also possible, if first dialyzing fluid pump 13 is not operated and therefore the inflow of dialyzing fluid into the dialyzing fluid chamber of the dialyzer is interrupted.

The device for monitoring the supply of substitution fluid comprises a control unit which, in the present example of embodiment, is part of central control and computing unit 18 of the blood treatment apparatus. Moreover, the device for detecting pre- and post-dilution comprises a measuring unit 21A for measuring the density of the blood or a blood constituent, which flows out of blood chamber 3 of dialyzer 2 via a venous blood line 7 back to the patient. Measuring unit 21A measures the density of the blood in venous blood line 7 downstream of venous admission point 20, at which substitution fluid flows into venous blood line 7 during the substitution.

Venous measuring unit 21A comprises an ultrasound transmitter 21A' and an ultrasound receiver 21A", which are disposed along a measuring distance. The measuring distance may for example run through a venous drip chamber (not shown) or through a section of the venous blood line following the drip chamber. Such ultrasound measuring devices for measuring the density of media are known to the person skilled in the art. The measuring devices are based on the measurement of the propagation speed of ultrasound waves, which are transmitted by transmitter 21A' and received by receiver 21A". Alternatively, a measuring unit for measuring the attenuation of light may be used to measure the blood instead of an ultrasound measuring device, said measuring unit comprising, instead of the ultrasound transmitter and receiver, a light source disposed on one side of the measuring distance and a light sensor disposed on the other side of the measuring distance.

The device for detecting pre- or post-dilution further comprises an evaluation unit 22, which is connected via a data line 23 to central control and computing unit 18. Evaluation unit 22 receives the measured values of measuring unit 21A via a further data line 24.

The structure and the mode of functioning of the device for detecting a pre- and post-dilution are explained in detail below.

During the extracorporeal blood treatment, central control and computing unit 18 controls blood pump 8 in such a way that blood flows into blood chamber 3 of the dialyzer at blood flow rate $Q_b$, and controls first and second dialyzing fluid pumps 13, 14 in such a way that dialyzing fluid flows into dialyzing fluid chamber 4 at dialyzing fluid rate $Q_{di}$ and dialyzing fluid flows out of dialyzing fluid chamber 4 at dialyzing fluid rate $Q_{do}$. Substituate pump 16 is controlled by control unit 18 in such a way that substitution fluid is fed to the blood optionally upstream and/or downstream of the blood chamber at substitution rate $Q_S$.

For the monitoring of pre- or post-dilution, control unit 18 controls substituate pump 16 in such a way that its delivery rate is preferably reduced by a preset amount only for a preset time interval or substituate pump 16 is stopped. At the same time, control unit 18 controls first and second dialyzing fluid pumps 13 and 14 in such a way that flow rate $Q_M$ at which fluid is withdrawn from the blood via membrane 2 of the dialyzer or filter, whereby $Q_M=Q_{do}-Q_{di}$, is simultaneously reduced within the same time interval by the same amount as the substitution rate has been reduced. The effect of this is that less fluid (ultrafiltrate) is removed from the blood via membrane 2 of dialyzer 1. Before and after the changing of the delivery rates or stopping of the pumps involved, measuring unit 21A measures the density of the blood or the blood constituent downstream of venous admission point 20.

It is also possible for substitution rate $Q_S$ and flow rate $Q_M$, at which fluid is withdrawn from the blood via the membrane of the dialyzer or filter, to be adjusted to a value of zero. This may be achieved, for example, by the fact that the dialyzer or filter is switched into a bypass operation, so that $Q_{di}$ is then also equal to zero. If there was previously a net ultrafiltration rate which has made a contribution to $Q_M$, flow rates $Q_S$ and $Q_M$ in this case are not reduced by the same amount, since $Q_M$ was greater than the net ultrafiltration amount.

Evaluation unit 22 comprises a comparison device 22A, which compares the value for the density of the blood or the blood constituent measured before the change in the delivery rates of the pumps with the value for the density measured immediately after the change in the delivery rates. The measurement of the density takes place within a specific time interval after the change in the flow rates, since the original values are re-established after the lapse of the time interval. The time interval should in any event be shorter than the length of the density change (rectangular function), empirical values being usable. It should be noted that the flow rate changes in the mentioned examples—$Q_S$ and $Q_M$ change by the same amount—lead only to a time-limited change in the density. On the basis of the change in the density, the evaluation unit then detects whether a dilution is taking place and ascertains whether a pre-dilution or post-dilution is present.

The operational states established by evaluation unit 22 are displayed on a display unit 25, which is connected via a data line 26 to evaluation unit 22. Furthermore, the evaluation unit generates two control signals, which on the one hand signal the operational state of pre-dilution and on the other hand the operational state of post-dilution. Both control signals are received by control unit 22 via data line 23, which may undertake an intervention into the machine control depending on the respective operational state of pre- or post-dilution.

In the case of post-dilution, evaluation unit 22 ascertains a short-time increase in the density of the blood at the measurement point. This is due to the fact that the blood has thickened after the passage through blood chamber 3 of dialyzer 1, since fluid (ultrafiltrate) has been withdrawn from the blood via membrane 2 of dialyzer 1. Since the already thickened blood in post-dilution is no longer diluted sufficiently with substitution fluid, the density of the blood or the blood constituent increases downstream of the dialyzer for a specific time period. The delivery rates need to be changed only for a short time for the measurement, i.e., the original delivery rates may be re-established after the measurement has taken place, as a result of which an opposite—again time-limited—behaviour of the density change occurs.

In the case of pre-dilution, on the other hand, the blood flowing into blood chamber 3 is diluted by the inflow of substitution fluid upstream of the blood chamber. Immediately after the time at which the delivery rates of the pumps are reduced, still diluted blood first enters into the blood chamber, from which, however, sufficient fluid is no longer withdrawn via the dialyzer membrane after the reduction in the delivery rates. Consequently, the density of the blood emerging from the blood chamber and flowing back to the patient diminishes. The reduction in the density is again measured with measuring unit 21 A, evaluation unit 22 establishing the operational state of pre-dilution.

Comparison device 22A of evaluation unit 22 calculates the difference between the two measured values of the density before and immediately after the change in the delivery rates. If the amount of the difference is greater than a preset threshold value, i.e., the values measured before and after the change in the substitution rate differ markedly from one another, evaluation unit 22 establishes that a dilution is taking place. Moreover, the evaluation unit ascertains whether an increase or decrease in the density is taking place, i.e., whether the difference between the measured values is positive or negative.

In the case of an increase in the density by an amount which is greater than a preset threshold value, the evaluation unit then ascertains the operational state of post-dilution. If the density has diminished by an amount whose magnitude is greater than a preset threshold value, the evaluation unit then ascertains the operational state of pre-dilution.

FIGS. 2A and 2B show the time-related course of the density of the blood in the case of pre-dilution (FIG. 2A) and post-dilution (FIG. 2B), substitution rate $Q_S$ on the one hand diminishing by a preset amount $\Delta Q_S < 0$ and flow rate $Q_M$ at which fluid is withdrawn from the blood diminishing simultaneously by the same amount.

The graphs of FIGS. 2A and 2B denoted by A show the time-related course of the density in the case of pre- or post-dilution, when the change in density is measured by measuring unit 21A downstream of venous admission point 20, as is described by reference to FIG. 1.

Alternative embodiments, however, also provide for a measurement of the change in density upstream of venous admission point 20 and downstream of blood chamber 3 or downstream of arterial admission point 19 and upstream of blood chamber 3 of dialyzer 1. Two further alternative measuring units are provided for this purpose, which are denoted in FIG. 1 by 21B and 21C. Measuring unit 21B measures the density upstream of venous admission point 20 and downstream of blood chamber 3, while measuring unit 21 C measures the density downstream of arterial admission point 19 and upstream of blood chamber 3.

The graphs of FIGS. 2A and 2B denoted by B show the time-related course of the density in the case of pre- (FIG. 2A) or post-dilution (FIG. 2B), when the change in density is measured with measuring unit 21 B, while graphs C show the time-related course of the change in density when the density is measured with measuring unit 21C.

It is shown that a variation in substitution rate $Q_S$, with a simultaneous change in $Q_M$, also leads to a change in the density of the blood upstream of venous admission point 20 and downstream of blood chamber 3. The density of the blood diminishes both in the case of pre- and post-dilution, the original value for the density being re-established in the case of pre-dilution, in contrast with post-dilution.

It may also be seen that a variation in substitution rate $Q_S$ also leads to a change in the density of the blood downstream of arterial admission point 19 and upstream of blood chamber 3. The density of the blood increases in the case of pre-dilution, whereas with post-dilution it neither increases nor decreases, i.e. it remains the same.

Alternative embodiments of the invention provide for a measurement of the change in density with measuring units 21B or 21C, the evaluation unit concluding that there is a pre- or post-dilution on the basis of the nature of the change in density, which is shown in FIGS. 2A and 2B. Suitable devices with which the signals may be evaluated are known to the person skilled in the art. These devices may comprise comparators, timers etc.

It is also possible to combine the aforementioned measuring methods with one another, so that a pre- or post-dilution may be detected on the basis of two or three measurements at different measurement points. For example, it may be concluded that there is a pre- or post-dilution if a change in the signals characteristic of a pre- or post-dilution is detected at least in two measurements at different measurement points.

FIGS. 3A (pre-dilution) and 3B (post-dilution) show the time-related course of the density of the blood or of a blood constituent, which is measured with measuring units 21A, 21B and 21C, when on the one hand substitute rate $Q_S$ is increased by a preset amount and simultaneously the flow rate at which fluid is withdrawn from the blood via membrane 2 is increased by the same amount. The graphs are again denoted, similar to FIGS. 2A and 2B, by A, B and C.

It may be seen that an increase in substitution rate $Q_S$, with a simultaneous change in $Q_M$, leads to a change in the density at all three measurements points in the case of pre-dilution. In contrast to a reduction in the rate, the consequence of an increase in $Q_S$ and $Q_M$ downstream of venous admission point 20 in the case of a pre-dilution is not to a reduction, but rather to an increase in the density and leads in the case of a post-dilution not to an increase, but rather a reduction in the density (graph A). The density increases upstream of venous admission point 20 and downstream of blood chamber 3 both for the pre- as well as the post-dilution, the original value for the density being re-established (graph B) in the case of pre-dilution, in contrast with post-dilution. The density in the case of pre-dilution diminishes downstream of arterial admission point 19 and upstream of blood chamber 3, whereas in the case of post-dilution it neither increases nor decreases, i.e. it remains the same (graph C).

In an alternative embodiment, control unit 18 and evaluation unit 22 are designed in such a way that substitution rate $Q_S$ and flow rate $Q_M$ are reduced and it is concluded that there is a pre- or post-dilution on the basis of the change in the density, as is described by reference to FIGS. 3A and 3B.

In a further example of embodiment, it is not substitution rate $Q_S$ or flow rate $Q_M$, but rather blood flow rate $Q_b$ that is changed (FIGS. 4A and 4B). Control unit 18 controls blood pump 8 in this embodiment in such a way that blood flow rate $Q_b$ is increased by a preset amount $\Delta Q_b$. Graphs A, B, C again show the time-related course of the density of the blood or the blood constituent, which is measured with the three measuring units 21A, 21B, and 21C. It may be seen that, with measuring units 21A and 21B, a pre- or post-dilution may be detected only with a more precise quantitative evaluation of the change in density. The evaluation unit therefore preferably evaluates the measured values of measuring unit 21C, with which the density downstream of arterial admission point 19 and upstream of blood chamber 3 of the dialyzer is measured. Evaluation unit 22 ascertains a pre-dilution if the density has increased by a preset amount and it ascertains a post-dilution if the density has not increased by a preset amount, i.e. has remained the same. It is of course also conceivable for blood flow rate $Q_B$ to be reduced by a preset amount. The measurements then run in each case in the opposite direction.

The invention claimed is:

1. A method for monitoring the supply of substitution fluid for an apparatus for extracorporeal blood treatment having a dialyzer or filter divided by a membrane into a first chamber and a second chamber, an extracorporeal blood circuit that includes the first chamber of the dialyzer or filter, and a fluid system that includes the second chamber of the dialyzer or filter, wherein blood is fed at a blood flow rate $Q_B$ to the first chamber of the dialyzer or filter and substitution fluid is fed to the blood at a substitution rate $Q_S$ upstream or downstream of the first chamber of the dialyzer or filter and fluid is withdrawn from the blood at a flow rate $Q_M$ via the membrane of the dialyzer or filter, the method comprising:
   changing at least one of a) the substitution rate $Q_S$, b) the blood flow rate $Q_B$, and c) the flow rate $Q_M$;
   measuring the density of the blood, or the density of a constituent of the blood, in the extracorporeal blood circuit; and
   detecting whether a supply of substitution fluid is upstream or downstream of the dialyzer or filter on the basis of a change in the density of the blood, or the density of the constituent of the blood, caused by the changing of the at least one of a) the substitution rate $Q_S$, b) the blood flow rate $Q_B$, and c) the flow rate $Q_M$.

2. The method according to claim 1, wherein, to perform the detecting of whether the supply of substitution fluid is upstream or downstream of the dialyzer or filter, the changing includes a) reducing the substitution rate $Q_S$ by a preset amount and reducing the flow rate $Q_M$, or b) increasing the substitution rate $Q_S$ and increasing the flow rate $Q_M$.

3. The method according to claim 2, wherein, to perform the detecting of whether the supply of substitution fluid is upstream or downstream of the dialyzer or filter, a) the substitution rate $Q_S$ is reduced by the same amount that the flow rate $Q_M$ is reduced, or b) the substitution rate $Q_S$ is increased by the same amount that the flow rate $Q_M$ is increased.

4. The method according to claim 1, wherein, after a reduction or increase in at least one of a) the substitution rate $Q_S$, b) the blood flow rate $Q_B$, and c) the flow rate $Q_M$ by a preset amount for a preset time interval, at least one of a) the substitution rate $Q_S$, b) the blood flow rate $Q_B$, and c) flow rate $Q_M$ is increased or reduced by a preset amount after the lapse of the preset time interval.

5. The method according to claim 1, wherein the density of the blood, or the density of the constituent of the blood, is measured in the blood circuit downstream of the point of the blood circuit at which the substitution fluid is fed to the blood circuit in the case of a pre-dilution.

6. The method according to claim 5, wherein the density of the blood, or the density of the constituent of the blood, is measured upstream of the first chamber of the dialyzer or filter.

7. The method according to claim 1, wherein the density of the blood, or the constituent of the blood, is measured downstream of the first chamber of the dialyzer or filter and upstream of the point of the blood circuit at which the substitution fluid is fed to the blood circuit in the case of a post-dilution.

8. The method according to claim 1, wherein the density of the blood, or the constituent of the blood, is measured downstream of the point of the blood circuit at which substitution fluid is fed to the blood circuit in the case of a post-dilution.

9. The method according to claim 1, wherein a propagation speed of an ultrasound in the blood along a measuring distance is measured for the measurement of the change in the density of the blood or the constituent of the blood.

10. The method according to claim 1, wherein an attenuation of light in the blood along a measuring distance is measured for the measurement of the change in the density of the blood or the constituent of the blood.

11. The method according to claim 1, wherein at least one of a) a signal signaling an operational state of pre-dilution is generated when it is concluded that there is a supply of substitution fluid upstream of the dialyzer or filter on the basis of the change in the density of the blood or the constituent of the blood, and b) a signal signaling an operational state of post-dilution is generated when it is concluded that there is a supply of substitution fluid downstream of the dialyzer or filter on the basis of the change in the density of the blood or the constituent of the blood.

12. A device for monitoring the supply of substitution fluid for an extracorporeal blood treatment apparatus that includes a) an extracorporeal blood circuit including a first chamber of a dialyzer or filter that is divided by a membrane into the first chamber and a second chamber, b) a fluid system that includes the second chamber of the dialyzer or filter, c) a device for supplying blood to the first chamber of the dialyzer or filter at a specific blood flow rate $Q_B$, d) a substitution device for supplying substitution fluid to the blood upstream or downstream of the dialyzer or filter at a specific substitution rate $Q_S$, and e) an ultrafiltration device for withdrawing fluid from the blood via the membrane of the dialyzer or filter at a specific flow rate $Q_M$, wherein the device for monitoring the supply of substitution fluid comprises:
   a measuring unit configured to measure the density of the blood, or the density of a blood constituent, in the blood circuit of the dialyzer or filter;

a control unit configured to control at least one of a) the substitution device, b) the device for supplying blood, and c) the ultrafiltration device, wherein the control unit is configured to change at least one of a) the substitution rate $Q_S$, b) the blood flow rate $Q_B$, and c) the flow rate $Q_M$ of the fluid withdrawn through the membrane of the dialyzer or filter; and an evaluation unit configured to conclude that there is a supply of substitution fluid upstream or downstream of the dialyzer or filter on the basis of the change in the density.

13. The device according to claim 12, wherein the control unit for controlling the substitution device is configured, for the detection of the supply of substitution fluid upstream or downstream of the dialyzer or filter, to a) reduce substitution rate $Q_S$ by a preset amount, while flow rate $Q_M$ of the fluid withdrawn through the membrane of the dialyzer or filter is reduced, or b) increase substitution rate $Q_S$ by a preset amount, while flow rate $Q_M$ of the fluid withdrawn through the membrane of the dialyzer or filter is increased.

14. The device according to claim 13, wherein the control unit for controlling the substitution device is configured, for the detection of the supply of substitution fluid upstream or downstream of the dialyzer or filter, to a) reduce substitution rate $Q_S$ by the same amount that flow rate $Q_M$ of the fluid withdrawn through the membrane of the dialyzer or filter is reduced, or b) increase substitution rate $Q_S$ by the same amount that flow rate $Q_M$ of the fluid withdrawn through the membrane of the dialyzer or filter is increased.

15. The device according claim 12, wherein the control device for controlling the substitution device is configured such that, after the reduction or increase in the at least one of a) the substitution rate $Q_S$, b) the blood flow rate $Q_B$, and c) the flow rate $Q_M$ of the fluid withdrawn through the membrane of the dialyzer or filter by a preset amount for a preset time interval, the at least one of a) the substitution rate $Q_S$, b) the blood flow rate $Q_B$, and c) the flow rate $Q_M$ of the fluid withdrawn through the membrane of the dialyzer or filter is increased or reduced after the lapse of the preset time interval.

16. The device according to claim 12, wherein the measuring unit is configured to measure the density of the blood or the blood constituent in the blood circuit downstream of the point of the blood circuit at which substitution fluid is fed to the blood circuit in the case of a pre-dilution.

17. The device according to claim 16, wherein the measuring unit is configured to measure the density of the blood or the blood constituent downstream of the point of the blood circuit at which substitution fluid is fed to the blood circuit in a pre-dilution, and upstream of the first chamber of the dialyzer.

18. The device according to claim 12, wherein the measuring unit is configured to measure the density of the blood or the blood constituent downstream of the first chamber of the dialyzer or filter and upstream of the point of the blood circuit at which substitution fluid is fed to the blood circuit in the case of a post-dilution.

19. The device according to claim 12, wherein the measuring unit is configured to measure the density of the blood or the blood constituent downstream of the point of the blood circuit at which substitution fluid is fed to the blood circuit in the case of a post-dilution.

20. The device according to claim 12, wherein the measuring unit is an ultrasound measuring device, which includes an ultrasound transmitter disposed at one end of a measuring distance and an ultrasound receiver disposed on the other end of the measuring distance for the measurement of the change in a propagation speed of ultrasound in the blood along the measuring distance.

21. The device according to claim 12, wherein the measuring unit is an optical measuring device, which comprises a light source disposed at one end of a measuring distance and a light sensor disposed at the other end of the measuring distance for the measurement of the attenuation of light in the blood along the measuring distance.

22. The device according to claim 12, wherein the control unit cooperates with the evaluation unit in such a way that the control unit at least one of a) generates a signal indicating an operational state of pre-dilution when it is concluded that there is a supply of substitution fluid upstream of the dialyzer or filter on the basis of the change in the density of the blood or the blood constituent, and b) generates a signal indicating an operational state of post-dilution when it is concluded that there is a supply of substitution fluid downstream of the dialyzer or filter on the basis of the change in the density of the blood or the blood constituent.

23. A blood treatment apparatus, comprising:
the device for detecting the supply of substitution fluid according to claim 12.

24. A blood treatment apparatus, comprising:
an extracorporeal blood circuit including a) a blood supply line leading to a first chamber of a dialyzer or filter that is divided by a membrane into the first chamber and a second chamber, the blood supply line configured to supply blood to the first chamber at a specific blood flow rate $Q_B$, and b) a blood discharge line leading away from the first chamber of the dialyzer or filter and away from the dialyzer or filter;
a fluid system connected to the second chamber of the dialyzer or filter;
a substitution device configured to supply substitution fluid to the blood at a specific substitution rate $Q_S$ via a first substituate line leading to a first admission point on that the blood supply line for supplying substitution fluid upstream of the dialyzer or filter and a second substituate line leading to a second admission point on the blood discharge line for supplying substitution fluid downstream of the dialyzer or filter,
an ultrafiltration device with which fluid can be withdrawn from the blood via the membrane of the dialyzer or filter at a specific flow rate $Q_M$; and
a device for monitoring the supply of substitution fluid including
a measuring unit configured to measure the density of the blood, or the density of a blood constituent, in the blood circuit of the dialyzer or filter,
a control unit configured to control at least one of a) the substitution device, b) the device for supplying blood, and c) the ultrafiltration device, wherein the control unit is configured to change at least one of a) the substitution rate $Q_S$, b) the blood flow rate $Q_B$, and c) the flow rate $Q_M$ of the fluid withdrawn through the membrane of the dialyzer or filter, and
an evaluation unit configured to conclude that there is a supply of substitution fluid upstream or downstream of the dialyzer or filter on the basis of the change in the density.

* * * * *